United States Patent [19]

McRae

[11] Patent Number: Plant 6,572

[45] Date of Patent: Jan. 31, 1989

[54] LILY PLANT NAMED FOXTROT

[75] Inventor: Edward A. McRae, Boring, Oreg.

[73] Assignee: Melridge, Inc., Aurora, Oreg.

[21] Appl. No.: 63,926

[22] Filed: Jun. 19, 1987

[51] Int. Cl.[4] ..... A01H 5/00
[52] U.S. Cl. ..... Plt./68
[58] Field of Search ..... Plt./68

*Primary Examiner*—James R. Feyrer
*Attorney, Agent, or Firm*—Charles W. Rummler

[57] ABSTRACT

A new variety of hybrid lily plant particularly characterized by the rich golden orange color of its relatively large blooms of excellent form, borne in large clusters and having a lack of spotting; thereby providing a combination that is completely new in the upright Asiatic divisions of lilies suited to forcing and to mass commercial cultivation. The plant is highly resistant to disease, shows high tolerance of virus, and is an excellent garden plant with bulbs that may be precooled and forced for cut flower production.

1 Drawing Sheet

BACKGROUND OF THE INVENTION

This new variety of lily plant originated as a seedling selected from a group of seedlings planted by me at Sandy, Oreg., with seeds from a hybrid developed by me by using a clonal cultivar of 'Connecticut King' as the seed parent and the clonal cultivar 'Croesus' as the pollen parent with the object of producing spotless upright Asiatic lilies in the shades of gold and orange, well suited to forcing for cut flower production out-of-season. This particular seedling was selected by me for proagation and test because of thelarge size of its blooms borne with an upright orientation with a rich golden orange coloration and a lack of spots. The selected seedling was asexually reproduced by me and under my direction at Sandy, Oreg., with such satisfactory results that propagation was continued under my direction through several successive generations, by bulb scale propagation and by natural propagation from bulblets, thereby demonstrating that the novel and distinctive characteristics of this new variety would hold true under asexual propagation from generation to generation and appearing to be firmly fixed.

Work with this new lily variety has demonstrated that the clone possesses to a high degree the desirable characteristics of hybrid vigor, great hardiness and disease resistance, as observed at Sandy, Oreg. Also, the new plant has been found to be well suited to forcing out-of-season when the bulbs are dug at the appropriate time and properly precooled. For example, October-dug bulbs properly precooled and potted in January will flower under glass in western Oregon in an average of seventy-five to eighty-five days, with no supplementary lighting and at moderate greenhouse temperatures.

DESCRIPTION OF THE DRAWING

This new variety of lily plant is illustrated by the accompanying photographic drawing, which shows the open bloom in full color and illustrates the flower form and tepal arrangement and in particular, the novel and distinctive large, rich golden orange coloration; the colors shown being as close to those specified herein as is reasonably possible to obtain by professional photographic procedures.

DESCRIPTION OF THE NEW VARIETY

The following is a detailed description of my new variety of Asiatic hybrid lily with nomenclature according to The International Lily Register of The Royal Horticultural Society of London, England, Second Edition, 1969; and with color designations according to The R.H.S. Colour Chart published by The Royal Horticultural Society in 1966.

THE PLANT

Origin: Seedling.

Parentage:

*Seed parent.*—Lilium 'Connecticut King' (unpatented).

*Pollen parent*—Lilium 'Croesus' (unpatented).

Classification:

*Horticultural.*—Division I-A, Upright Asiatic Hybrid Lily, according to The Horticultural Classification of Lilies (The Royal Horticultural Society of London).

*Commercial.*—Hybrid Lilium Clone.

Form: A single stem, erect and stately.

Height: About 80 to 100 cm. from bulbs of about 15 to 18 cm. in circumference, provided that the light levels are adequate; low light levels may cause "stretching".

Growth: Vigorous and upright.

Foliage:

*Quantity.*—Abundant.

*Size of leaf.*—About 8 to 10 cm. long and about 0.7 to 1 cm. in width.

*Leaf shape.*—Lanceolate with acuminate tip.

*Texture.*—Leathery.

*Aspect.*—Glossy.

*Color.*—Deep green, lighter on the under side.

The bulbs:

*Size.*—Various, ranging to 25 cm. in circumference as commercially used.

*Color.*—White.

THE BUD

Form: Long ovoid with obtuse apex and rounded base.

Size: About 8 to 9 cm. long and about 7 cm. in circumference just prior to opening.

Opening rate: The bud opens slowly, taking about one hour in response to morning light.

Color: Soft Orange, 25C/D, overlaid with soft green just prior to opening and as the tepals begin to unfurl.

Peduncle:

*Length.*—Averages about 4 to 6 cm., but may elongate if light levels are too low or if the bulbs have been improperly stored prior to forcing.

*Color.*—Dark green with a plum overlay.

THE FLOWER

Blooming habit: Once annually and profusely in midseason.

Size: Large; about 16 to 18 cm. in diameter.

Borne: In a single, compact raceme having 8 to 11 buds from a bulb of about 18 cm. in circumference.

Shape: Cup-shaped when first opening and flattening as the tepals recurve during the second day.

Tepalage: Typical of genus Lilium with six imbricated tepals in hexagonal arrangement. The tepals are "clawed", narrow at the base but broader at the midpoint of their length, the outer tepals being of about 2 to 2.5 cm. in width and the inner tepals being about 3 cm. wide.

*Color.*—The base of the tepals is Orange, 25B/C, shading to 28A/B along the tepal margins, at the apex, and just above the nectaries. The nectaries are soft orange overlaid with short, white pubescence.

*Spotting.*—The tepals are spotless.

*Aspect.*—Shiny.

Pedicel:

*Length.*—Averages about 6 to 10 cm.

*Character.*—Sturdy and ascending up to about 45 degrees from the horizontal.

*Color.*—Dark green with plum overlay.

Secondary buds: Very rare.

Tepal longevity: The tepals stay on the stems for about three weeks.

Color changes: The color may change slightly becoming more orange as the flower ages; the color may be slightly lighter under conditions of low light and there is little change in flower color under light conditions adequate for cut flower maintenance.

Fragrance: None.

Lasting quality: The flowers are long lasting, both on the plant and as a cut flower.

Disease resistance: The flower and plant are resistant to disease; and in particular, they are resistant to Fusarium bulb rot and Botrytis blight as observed in western Oregon.

REPRODUCTIVE ORGANS

Stamens:

*Number.*—Six.

*Arrangement.*—Typical of genus Lilium.

*Anthers (dehisced) and pollen.*—Color: Orange-Red, 34B.

*Filaments.*—Length: About 5 cm. Color: Soft Orange, 28B/C.

Pistil:

*Number.*—One.

*Length.*—About 5 cm.

*Stigma.*—Color: Soft Orange, 180B/C, with a light plum overlay.

Character of ovary: The ovary is characteristic of the genus Lilium.

THE FRUIT

Fertility: The fruit is fertile.

Shape: Ovoid.

Color at maturity: Soft brown, sometimes overlaid with soft plum.

This new variety of Asiatic hybrid lily most nearly resembles 'Croesus' (unpatented) but it has larger flowers with no spotting, clawed tepals which are broader at midpoint and have a richer color. The new variety also has a more compact inflorescence and is more reliable when forced into flower out-of-season than is the variety 'Croesus'.

I claim:

1. The new and distinctive variety of Asiatic hybrid lily plant and parts thereof substantially as herein shown and described, characterized by its large, broad but "clawed" tepalled flowers of rich golden orange coloration which are completely unspotted; by the excellence of its flower form, its vigorous growth and rapid natural propagation, and its versatility both as a garden plant and as a cut flower producer from precooled bulbs forced under glass out-of-season.

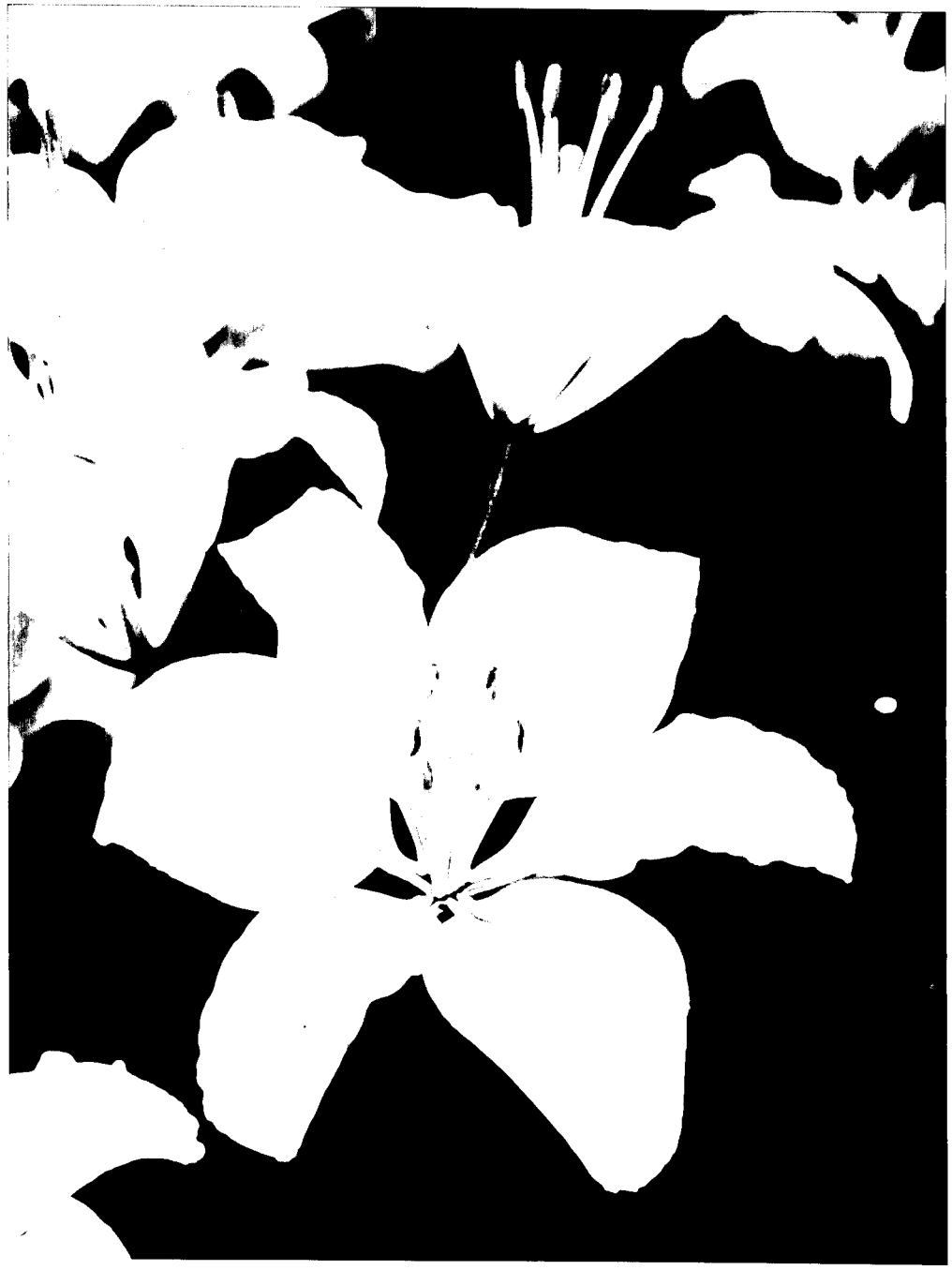

* * * * *